US009855104B2

(12) United States Patent
Blau et al.

(10) Patent No.: US 9,855,104 B2
(45) Date of Patent: Jan. 2, 2018

(54) LOCKING SCREW LENGTH MEASUREMENT

(75) Inventors: Arno Blau, Staufen Im Breisgau (DE); Bernd Simon, Kiel (DE); Nils Reimers, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 518 days.

(21) Appl. No.: 14/401,715

(22) PCT Filed: May 23, 2012

(86) PCT No.: PCT/EP2012/002207
§ 371 (c)(1),
(2), (4) Date: Feb. 6, 2015

(87) PCT Pub. No.: WO2013/174402
PCT Pub. Date: Nov. 28, 2013

(65) Prior Publication Data
US 2015/0164445 A1    Jun. 18, 2015

(51) Int. Cl.
*A61B 17/34* (2006.01)
*A61B 17/12* (2006.01)
(Continued)

(52) U.S. Cl.
CPC ............ *A61B 34/10* (2016.02); *A61B 6/12* (2013.01); *A61B 6/505* (2013.01);
(Continued)

(58) Field of Classification Search
CPC ........... A61B 6/12; A61B 6/505; A61B 34/10; A61B 2034/101; A61B 2034/102;
(Continued)

(56) References Cited

U.S. PATENT DOCUMENTS 4,106,128 A    8/1978   Greenwald et al.
5,398,684 A    3/1995   Hardy
(Continued)

FOREIGN PATENT DOCUMENTS

EP    2363083 A1    9/2011
WO    2004069040 A2    8/2004
(Continued)

OTHER PUBLICATIONS

Schulz et al., "Evidence Based Development of a Novel Lateral Fibula Plate (VariAx Fibula) Using a Real CT Bone Data Based Optimization Process During Device Development", The Open Orthopaedics Journal, 2012, 6, 1-7.
(Continued)

*Primary Examiner* — Christian Sevilla
*Assistant Examiner* — Eric S Gibson
(74) *Attorney, Agent, or Firm* — Lerner, David, Littenberg, Krumholz & Mentlik, LLP (57) ABSTRACT

A method and device is provided for identifying a length of a bone screw to be inserted through a bore drilled in a predetermined drilling direction at a predetermined position through a bone. The predetermined drilling direction and the predetermined position is identified in an X-ray projection image of the bone, and the identified direction and position is transferred to a corresponding model of the imaged bone, wherein the bone model is a 3D model. The length of the bone screw is finally determined at the bone model based on the transferred direction and position.

13 Claims, 5 Drawing Sheets (51) Int. Cl.
*A61B 34/10* (2016.01)
*A61B 6/12* (2006.01)
*A61B 6/00* (2006.01)
*A61B 17/86* (2006.01)
*A61B 17/17* (2006.01)
*A61B 17/72* (2006.01)
*A61B 90/00* (2016.01)

(52) U.S. Cl.
CPC .......... *A61B 17/1725* (2013.01); *A61B 17/72* (2013.01); *A61B 17/86* (2013.01); *A61B 2034/105* (2016.02); *A61B 2034/108* (2016.02); *A61B 2090/061* (2016.02)

(58) Field of Classification Search
CPC ........ A61B 2034/105; A61B 2034/107; A61B 2034/108; A61B 90/06; A61B 2090/061
USPC ........................................................ 606/102
See application file for complete search history.

(56) References Cited

U.S. PATENT DOCUMENTS

| | | | |
|---|---|---|---|
| 5,799,055 | A | 8/1998 | Peshkin et al. |
| 6,064,932 | A | 5/2000 | François |
| 6,198,794 | B1 | 3/2001 | Peshkin et al. |
| 6,470,207 | B1 | 10/2002 | Simon et al. |
| 6,682,565 | B1 | 1/2004 | Krishnan |
| 6,701,174 | B1 | 3/2004 | Krause et al. |
| 6,711,432 | B1 | 3/2004 | Krause et al. |
| 9,119,722 | B1 | 9/2015 | Kusuma |
| 2004/0068187 | A1 | 4/2004 | Krause et al. |
| 2004/0111024 | A1* | 6/2004 | Zheng ................. A61B 6/4441 600/426 |
| 2004/0240715 | A1 | 12/2004 | Wicker et al. |
| 2005/0251113 | A1* | 11/2005 | Kienzle, III ....... A61B 17/1703 606/1 |
| 2006/0015188 | A1 | 1/2006 | Grimes |
| 2007/0270680 | A1 | 11/2007 | Sheffer et al. |
| 2008/0075348 | A1* | 3/2008 | Rappaport ............ A61B 5/107 382/132 |
| 2008/0175464 | A1 | 7/2008 | Brett et al. |
| 2008/0294265 | A1 | 11/2008 | Warkentine et al. |
| 2008/0319448 | A1 | 12/2008 | Lavallee et al. |
| 2009/0017430 | A1* | 1/2009 | Muller-Daniels ...... G09B 23/30 434/262 |
| 2009/0209851 | A1* | 8/2009 | Blau ................. A61B 17/1703 600/426 |
| 2010/0241129 | A1 | 9/2010 | Markey et al. |
| 2011/0082367 | A1* | 4/2011 | Regazzoni ............ A61B 34/20 600/425 |
| 2011/0092804 | A1 | 4/2011 | Schoenefeld et al. |
| 2011/0213379 | A1* | 9/2011 | Blau ................. A61B 17/1703 606/102 |
| 2012/0106819 | A1* | 5/2012 | Fernandez Oca ...... A61B 34/10 382/132 |
| 2013/0211386 | A1* | 8/2013 | Blau ................. A61B 17/1703 606/1 |
| 2013/0317512 | A1* | 11/2013 | Buhren ................. A61B 34/20 606/102 |
| 2015/0164445 | A1* | 6/2015 | Blau ........................ A61B 6/12 606/102 |
| 2015/0265361 | A1* | 9/2015 | Blau ................. A61B 17/1703 606/67 |
| 2016/0278824 | A1* | 9/2016 | Toy ..................... A61B 17/1728 |
| 2016/0296285 | A1* | 10/2016 | Chaoui .................. A61B 34/10 |
| 2016/0354156 | A1* | 12/2016 | Blau .................. A61B 17/1725 |

FOREIGN PATENT DOCUMENTS

| | | | |
|---|---|---|---|
| WO | 2010121147 | A1 | 10/2010 |
| WO | 2010122145 | A1 | 10/2010 |

OTHER PUBLICATIONS

Extended European Search Report for Application No. EP12169104 dated Sep. 3, 2012.
Dahlen et a. "Computer-assistierte OP-Planung", Der Unfallchirurg, vol. 104, No. 6, Jun. 1, 2001 (Jun. 1, 2001), pp. 466-479, XP55036111.
Zheng et al, "Reality-augmented virtual fluoroscopy for computer-assisted diaphyseal long bone fracture osteosynthesis: a novel technique and feasibility study results", Proceedings of the Institution of Mechanical Engineers.Journal of Engineering in Medicine. Part H, Mechanical Engineering Publications LTD, London, GB, vol. 222, No. H1, Jan. 1, 2008 (Jan. 1, 2008), pp. 101-115, XP009162175.
Guoyan Zheng et al, "A hybrid CT-free navigation system for total hip arthroplasty", Computer Aided Surgery, vol. 7, No. 3, Jan. 1, 2002 (Jan. 1, 2002), pp. 129-145, XP55036140.
International Search Report and Written Opinion for Application No. PCT/EP2012/002207 dated Feb. 8, 2013.
International Search Report for Application No. PCT/EP2012/002206 dated Feb. 12, 2013.
Image Registration Defined Archived on Apr. 2012 downloaded from https://en.wikipedia.org/w/index.php?title=Image_registration&oldid=488834006.

* cited by examiner

LOCKING SCREW LENGTH MEASUREMENT

CROSS-REFERENCE TO RELATED APPLICATIONS

The present application is a national phase entry under 35 U.S.C. §371 of International Application No. PCT/EP2012/002207 filed May 23, 2012, published as WO 2013/174402 A1, the disclosure of which is hereby incorporated herein by reference.

FIELD OF THE INVENTION

The invention relates to the field of computer assisted surgery. Particularly, the invention relates to a computer software based method for identifying a length of a bone screw to be inserted through a bore in a bone. Furthermore, the invention relates to a corresponding device and to a method of operating the same.

BACKGROUND OF THE INVENTION

Usually, a bone screw and in particular a locking screw for fixating a bone nail is inserted into a bone by opening the tissue surrounding the bone, to achieve an access to the bone at a site at which it is intended to introduce a screw. Before screwing in the screw, a bore is drilled into the bone forming a channel for the screw. Into such a channel, a bone screw may be screwed in.

A critical aspect of such an insertion of a bone screw is that the screw should have a length which is long enough to provide sufficient stability, i.e. as much as possible of the thread of the screw should engage with hard bone tissue (Corticalis), but the screw should, on the other hand, have a length which is not too long so that at least one end section of the screw may protrude out of the bone which may cause irritations and insurances at the surrounding soft tissue, i.e. muscles or sinews. Having in mind that a physician will usually have access to a bone only from one side, i.e. at the entry point for the screw, it is difficult to measure the length or depth of a bore into which a screw should be introduced.

SUMMARY OF THE INVENTION

It may be seen as an object of the invention to provide means for identifying a length of a bone screw to be inserted through a bore in a bone, for assisting an insertion of a screw and for achieving better implantation results. A further object may be to reduce the amount of radiation to which a patient is exposed during an implantation procedure. These and other objects will be solved by the subject-matter of each of the independent claims. Further embodiments are described in the respective dependent claims.

According to a first aspect, a method comprises, in general, the steps of identifying a predetermined or intended drilling direction and a predetermined or intended position in a first X-ray projection image of the bone, transferring the identified direction and position to a corresponding 3D bone model, and determining the length of the bone screw at the bone model, based on the transferred direction and position.

As use herein, in addition to any plain and ordinary meaning, the term "bone model" encompasses, for example, a 3D model of a bone. The bone model may be generated based on at least one 3D scan of at least one real bone of the same kind, for example a femur or humerus, and/or by forming an average from a plurality of 3D scans. An exemplary utilization of bone models is described in 'Evidence based development of a novel lateral fibula plate (VariAX Fibula) using a real CT bone data based optimization process during device development' of A. P. Schulz et al. (The Open Orthopaedics Journal, 2012, 6, 1-7), the content of which is incorporated herein by reference.

Various dimensions from a corresponding 3D model are utilized to calculate the screw length along different directions and positions not shown in the x-ray of the bone to be treated. It has been found that there is a very high probability that the corresponding 3D model matches the bone to be treated with sufficient accuracy for determining acceptable screw length approximations.

In other words, based on only one projection image it is thus possible to determining a length between two points wherein at least one of these points is obscured, i.e. not visible in the projection image. For example, it is possible to determining the length between two outer surfaces, measured in the imaging direction. In other words, a depth of a structure may be determined in a projection image of the structure.

According to an embodiment, the identification of the predetermined position at the bone includes a measurement of the distances between the bore and the outer surface of the imaged bone (i) in an axial direction of the bone and (ii) in a direction perpendicular to the axial direction of the bone.

That is, the position of the center point of the bore axis, when looking in the direction of the bore axis, is measured in a longitudinal direction and a transverse direction of the bone. It will be understood that the direction of the bore axis is identical to the drilling direction.

According to a further embodiment, the method further comprises the step of determining a diameter of the imaged bone between two opposed outer surfaces of the imaged bone in relation to a reference body which is also visible in the X-ray image. The diameter may be the distance between both outer bone surfaces in a transverse direction of the bone, preferably in the same transverse direction as the transverse direction in which the position of the bore is identified or measured.

It is noted that the dimensions of the reference body will be known so that a factor can be calculated representing the relation between, for example, a length of the reference body as imaged and an actual length of the reference body. This factor may subsequently be used to determine for example an actual diameter of an imaged bone. The actual diameter of the imaged bone may in turn lead to a bone model, wherein at least the size of the bone model fits to the imaged bone so that a length which is not visible in the image can be determined at the bone model.

A particular bone like a femur has an almost constant relation between its length and its width, i.e. the femur has a specific shape regardless of its size. Therefore, a bone model can be selected based on only one measured dimension, for example a diameter of the shaft in one direction. It can be assumed as very likely that other dimensions of the bone model like the length or a diameter perpendicular to the measure diameter correlate to the corresponding actual dimensions of an imaged bone.

It is noted that the data of the first X-ray image may be received directly from an imaging device, for example from a 2D C-arm based X-ray device. The image may represent an anatomical structure of interest, in particular a bone.

According to another embodiment, the method further comprises the step of selecting a bone model from a group of bone models with different sizes and shapes, the selected bone model corresponding to the imaged bone. The group of bone models may be stored in a database. Further, the group of bone models may be a selection of previously generated 3D images, each of another person, wherein the persons may differ in size, weight and age. The database may thus contain several models of each bone (e.g. tibia, femur, humerus) including bone models of different ages, genders and individual sizes. The software uses gray scale image data to determine at least one dimension from the x-ray (2D image) of the bone to be treated and searches the database for a bone model of a person of the same age, gender and size, for example, having an identical or at least a close approximation to the at least one dimension from the bone to be treated. When a match is determined a three dimensional model of the matched bone in the database is selected and utilized as a corresponding 3D bone model of the bone to be treated.

According to yet another embodiment, the method further comprises the step of adapting a bone model so that the bone model corresponds to the imaged bone. Also here, the bone model may be stored in a database. In this case, the bone model may be generated by forming an average of a plurality of previously generated 3D images. To adapt the bone model to the imaged bone, substantially the size of the bone model may be increased or decreased so as to fit to the size of the bone as measured in the image.

According to an embodiment, the first X-ray image is generated in a direction being parallel to the drilling direction. Thus, the first X-ray image is generated from a point of view from which one may look in a direction in which the axis of the bore extends, i.e. one may look for example perpendicular onto the bone. From such a point of view it may be easier to identify outer surfaces of the bone and to measure a distance from a distinct outer surface to the center of the bore.

In case of a locking screw for locking a bone nail, the length of the bone screw may correspond to the distance between the outer surfaces of the bone at both ends of the bore with the bore being a through bore through a long bone.

An improved result may be achieved based on a second X-ray image generated from a second imaging direction. Accordingly, the method may further comprises the step of determining a diameter of the imaged bone between two opposed outer surfaces of the imaged bone in relation to the reference body which is also visible in a second X-ray image of the bone, wherein the imaging directions of the first X-ray image and the second X-ray image differ from each other.

Although the shape of one bone, for example a femur, does usually not vary with an increasing size, at least as a first approximation, sometimes the shape may not be as expected. Therefore, a second X-ray image may serve as a means to control the expected dimensions of an imaged bone to ensure that the used bone model fits both in size and shape to the imaged bone.

According to a further embodiment, the method does not include any step leading to a situation in which a bone nail is positioned in a bone, in so far as the step constitutes a treatment of a human or animal body by surgery.

According to a further aspect, a device for identifying a length of a bone screw to be inserted through a bore drilled in a predetermined drilling direction at a predetermined position through a bone, comprises a processing unit adapted for executing the above described method, i.e. comprises a processing unit adapted for identifying the predetermined direction and the predetermined position at the bone in an X-ray image, transferring the identified direction and position to a corresponding bone model, and determining the length of the bone screw based on the transferred direction and position at the bone model.

According to an embodiment, the device comprises storage means providing a database. It will be understood, that such storage means may also be provided in a network to which the system may be connected and information related to the bone model, i.e. different types of models and parameter thereof, may be received over that network.

Furthermore, the device may comprise an imaging unit for generating the at least one X-ray image, wherein the imaging unit may be capable of generating images from different directions.

The device may further comprise input means for manually determining a position in the X-ray image, for example a bone surface, for measuring a distance in the image. Such input means may be for example a computer keyboard, a computer mouse or a touch screen, to control a pointing device like a cursor on a monitor screen which may also be included in the device.

According to yet another embodiment, the processing unit is further adapted for adapting the bone model so that the bone model corresponds to the imaged bone.

It is noted, that the processing means may be realized by only one processor performing all the described steps, or by a group or plurality of processors, for example a system processor for processing the image data including an identification of anatomical structures like a bone surface, a separate processor specialized on processing of a bone model and determining distances, and a further processor for controlling a monitor for visualizing the result.

According to another aspect, a computer software is provided, which when executed on a device as described, causes the device to perform the steps of the method as described.

The computer software may include sets of instructions for determining a position on a bone surface and/or a diameter between outer surfaces so that such determination may be performed automatically. It will be understood that the computer program may further include sets of instructions to identify a reference object in the image.

A corresponding computer program may preferably be loaded into a work memory of a data processor. The data processor or processing unit may thus be equipped to carry out at least a part of the described method. Further, the invention relates to a computer-readable medium such as a CD-ROM at which the computer program may be stored. However, the computer program may also be presented over a network like the World Wide Web and can be downloaded into the working memory of the data processor from such a network.

It has to be noted that embodiments are described with reference to different subject-matters. In particular, some embodiments are described with reference to method type claims (computer program) whereas other embodiments are described with reference to apparatus type claims (device). However, a person skilled in the art will gather from the above and the following description that unless other notified in addition to any combination of features belonging to one type of subject-matter also any combination between features relating to different subject-matters is considered to be disclosed with this application.

The aspects defined above and further aspects, features and advantages of the present invention can also be derived from the examples of the embodiments to be described hereinafter and are explained with reference to examples of embodiments also shown in the figures, but to which the invention is not limited.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF THE EMBODIMENTS

Figure 1:
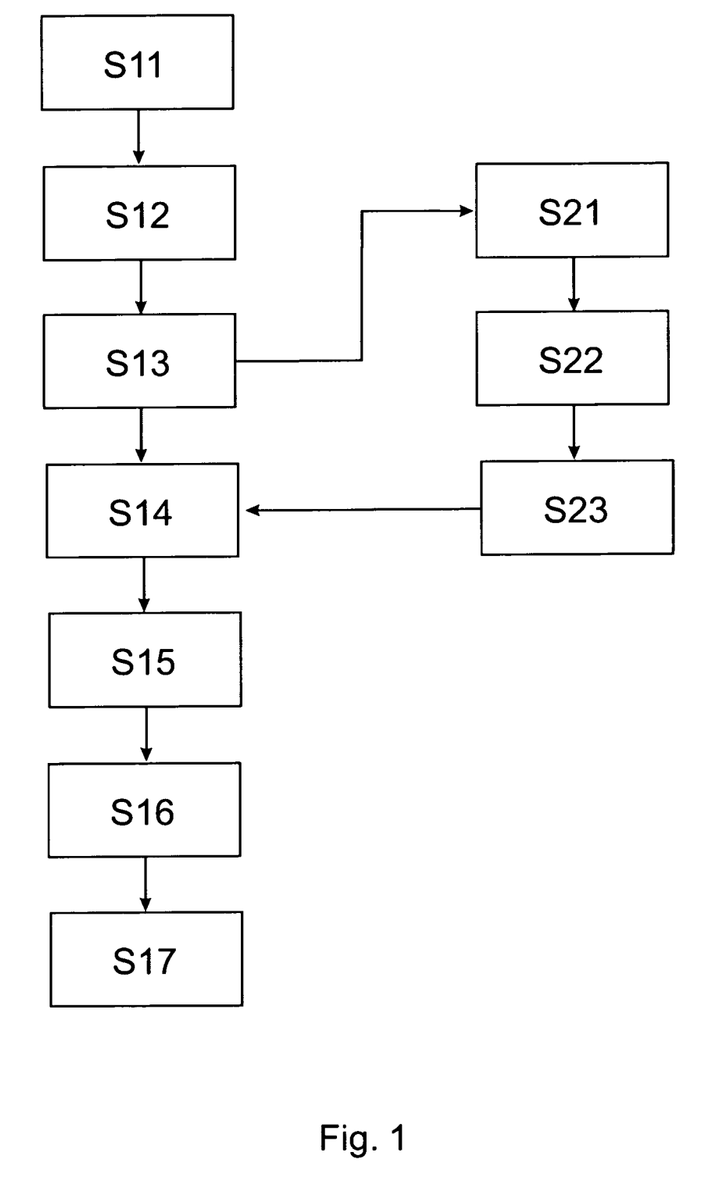
FIG. 1 shows a flow chart of steps performed in accordance with a method described herein.

The flow-chart in FIG. 1 illustrates the principle of the steps performed in accordance with the described method. It will be understood that the steps described, are major steps, wherein these major steps might be differentiated or divided into several sub-steps. Furthermore, there might be also sub-steps between these major steps.

In step S11, a first X-ray image is received, wherein this X-ray image may be generated for example in a medial-lateral direction. The first X-ray image shows a region of interest including a position at a bone into which a screw is to be inserted. The X-ray image further shows a reference body.

In step S12, a scale factor is determined based on the actual and the imaged dimensions of the reference body.

In step S13, a first dimension of the bone is measured in the X-ray image and the corresponding first dimension of the actual bone is determined.

In step S14, a 3D bone model is selected or adapted, at least the first dimension of which fits to the first dimension of the actual bone.

In step S15, the location on the bone surface at which a bone screw should be inserted as well as a drilling direction is identified. It will be understood that the drilling direction may be easy identified in a case in which a tissue protection sleeve is visible in the X-ray image. As already mentioned, a bore will be provided in the drilling direction into which a bone screw may subsequently be screwed in.

In step S16, the identified point and direction is transferred to the selected and/or adapted bone model.

In step S17, a distance is measured at the 3D bone model, the distance representing an appropriate length for a screw which thus can be accurately inserted into the bone at the identified position and in the identified direction.

Following step S13, a second X-ray image may be received in step S21. The second X-ray image should be generated from an imaging direction which is different to the imaging direction of the first X-ray image. For example, the second X-ray image may be generated in an anterior-posterior direction. As the first X-ray image, the second X-ray image shows the region of interest as well as a reference body.

In step S22, a further scale factor is determined based on the actual and the imaged dimensions of the reference body. It is noted that the further scale factor may be utilized for all dimensions related to the projection plane of the second X-ray image. In this case, the scale factor as determined in step S12 may thus only be utilized for the dimensions related to the projection plane of the first X-ray image.

In step S23, a second dimension of the bone is measured in the second X-ray image and the corresponding second dimension of the actual bone is determined.

Following step S23, a 3D bone model is selected or adapted in step S14, wherein in this case the first and second dimensions as well as both scale factors are taken into account. Subsequently, steps S15 to S17 are performed as described above.

By way of the described methods, a physician may be provided with information supporting the decision which bone screw should be used.

Figure 2:
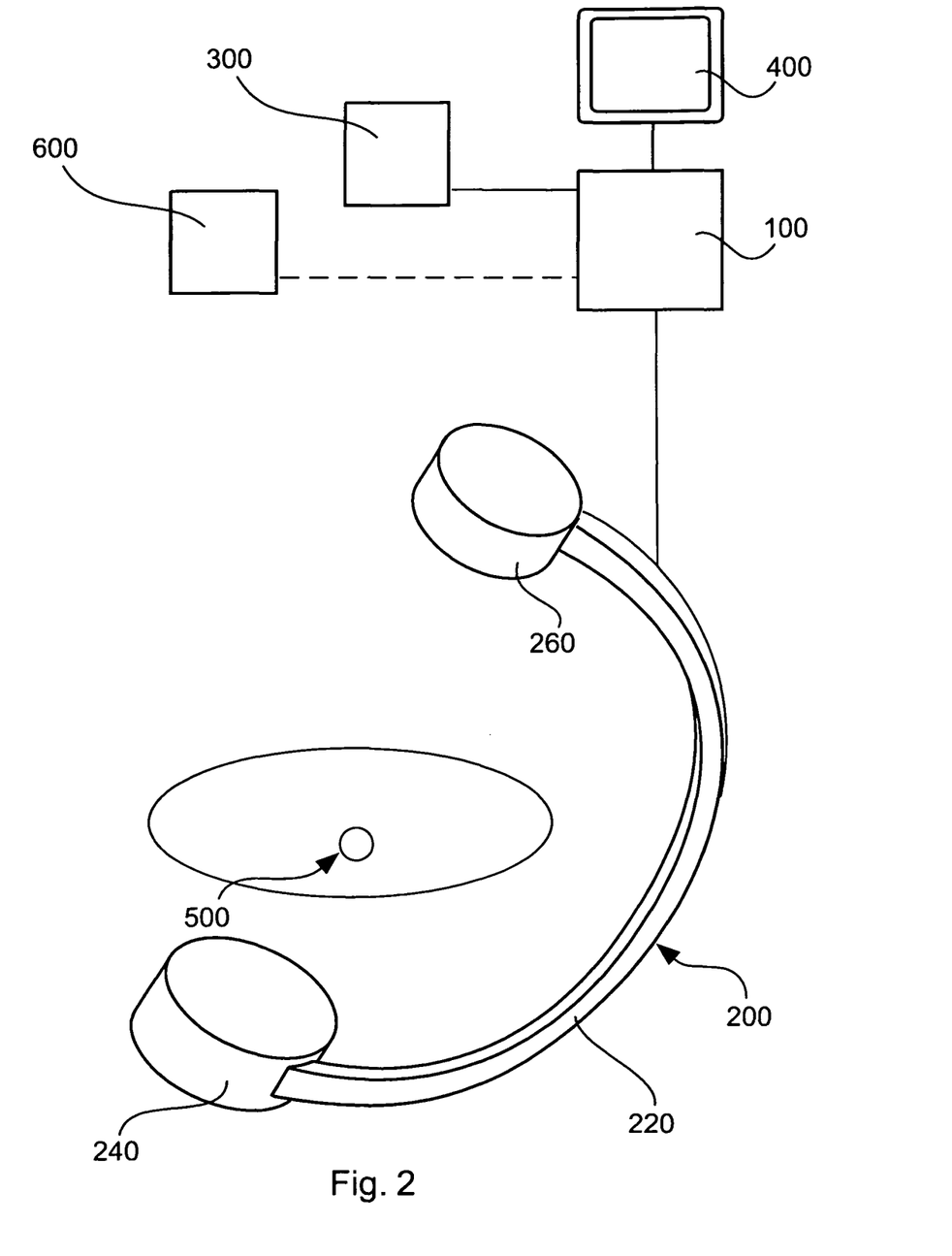
FIG. 2 shows a schematical illustration of a system according to an embodiment described herein.

FIG. 2 shows an embodiment of a device. Substantially necessary for performing the described steps, the device comprises a processing unit 100 and a monitor 400.

The exemplary imaging device 200 includes an X-ray source 240, and an X-ray detector 260, wherein these two devices are mounted on a C-arm 220. It will be understood that the device may also comprise another non-invasive imaging modality like a computer tomography device as imaging device instead of or additional to the shown C-arm based X-ray device, to generated individual projection images.

Furthermore, the device in FIG. 2 includes an input device 300, by means of which for example a manual determination of a position on a bone surface may be performed. Also shown is a connection (as dotted line) to a database 600, located for example in a network.

Finally, there is shown a region of interest 500. Within said region, for example a bone of a patient may be located, wherein it is intended to introduce a screw into that bone, but an appropriate length of the screw has to be identified.

Figure 3:
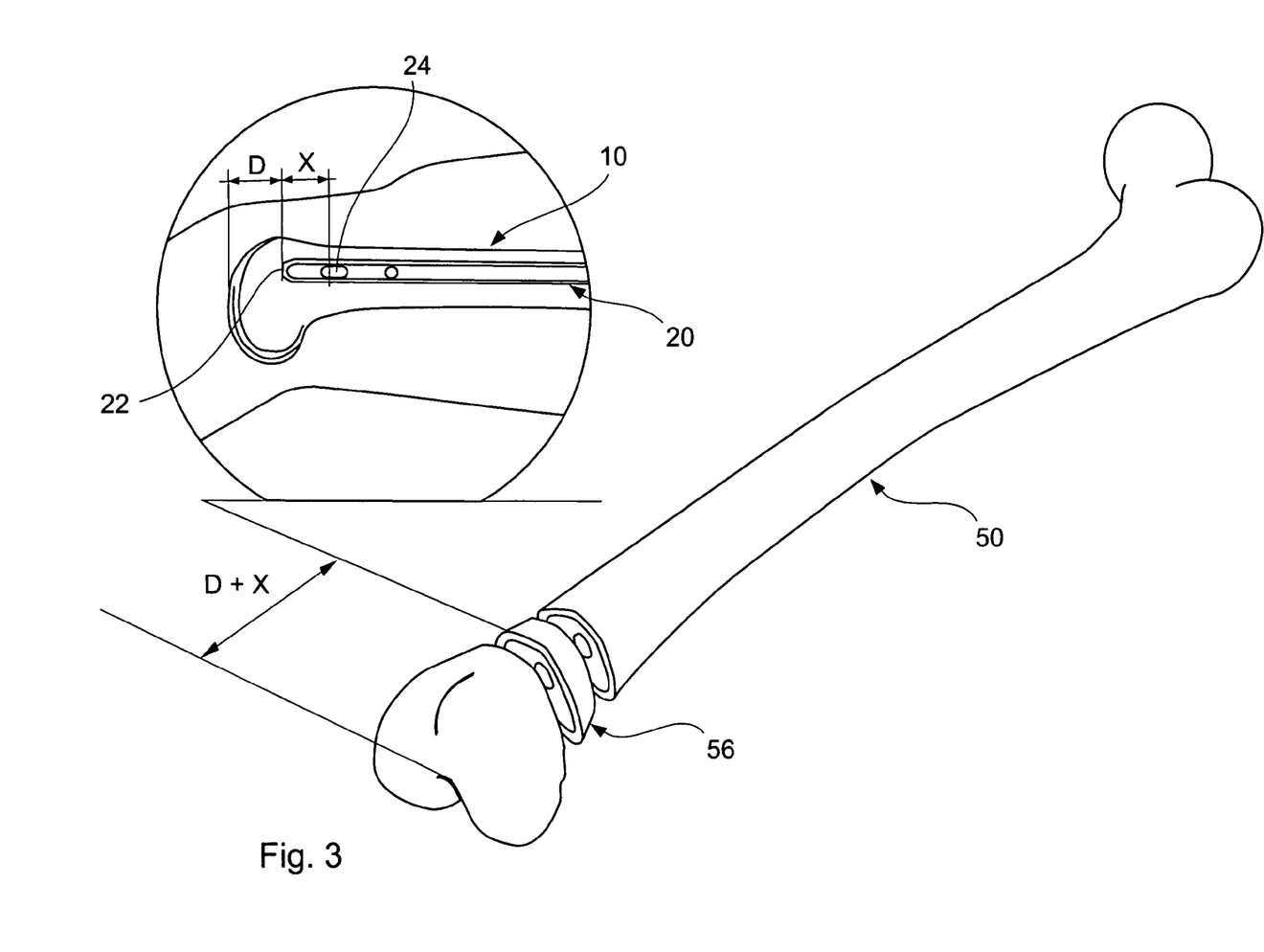
FIG. 3 illustrates a transfer of a distance in a longitudinal direction from an imaged bone to a bone model.
Figure 4:
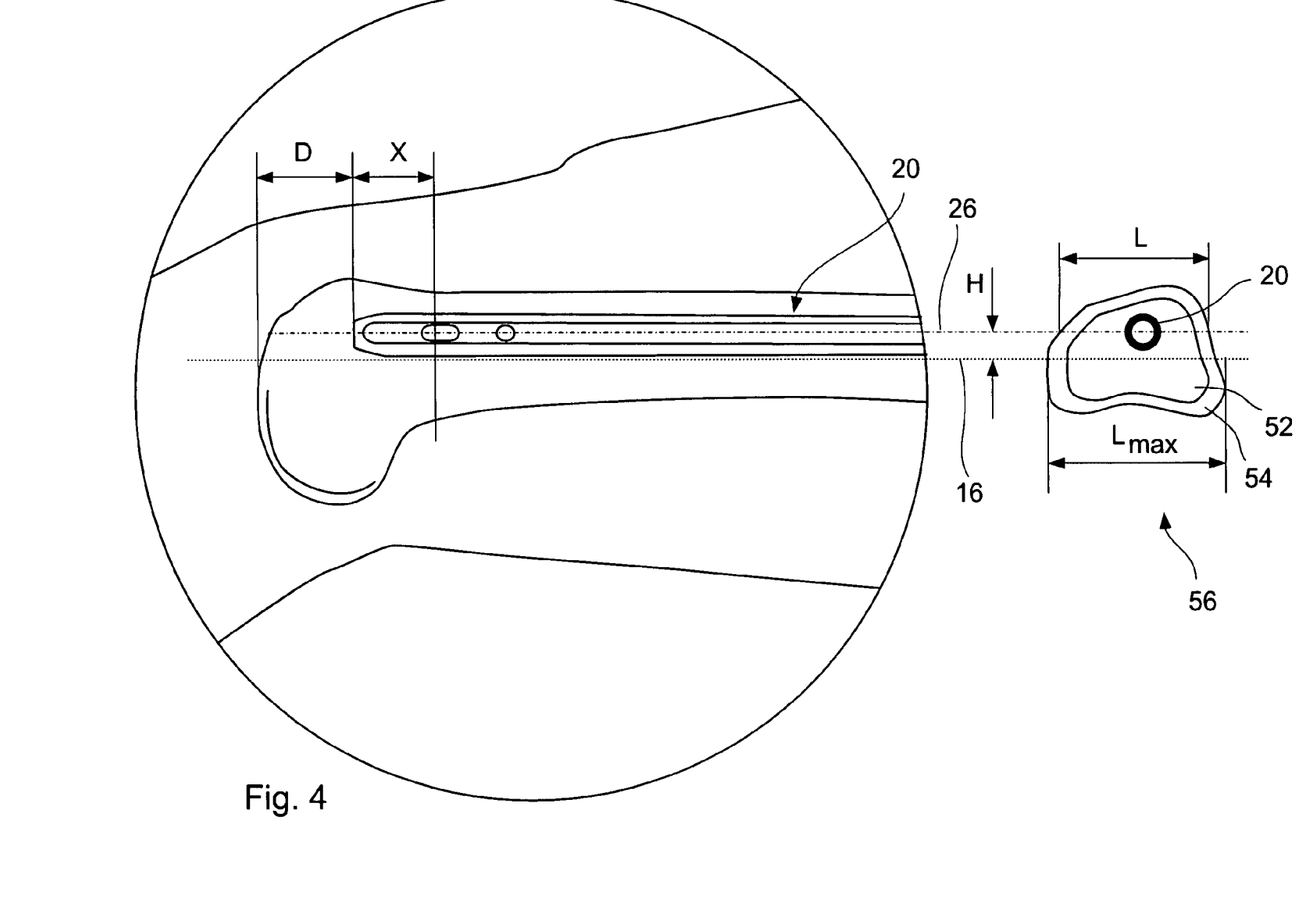
FIG. 4 illustrates a transfer of a distance in a transverse direction from an imaged bone to a bone model.
Figure 5:
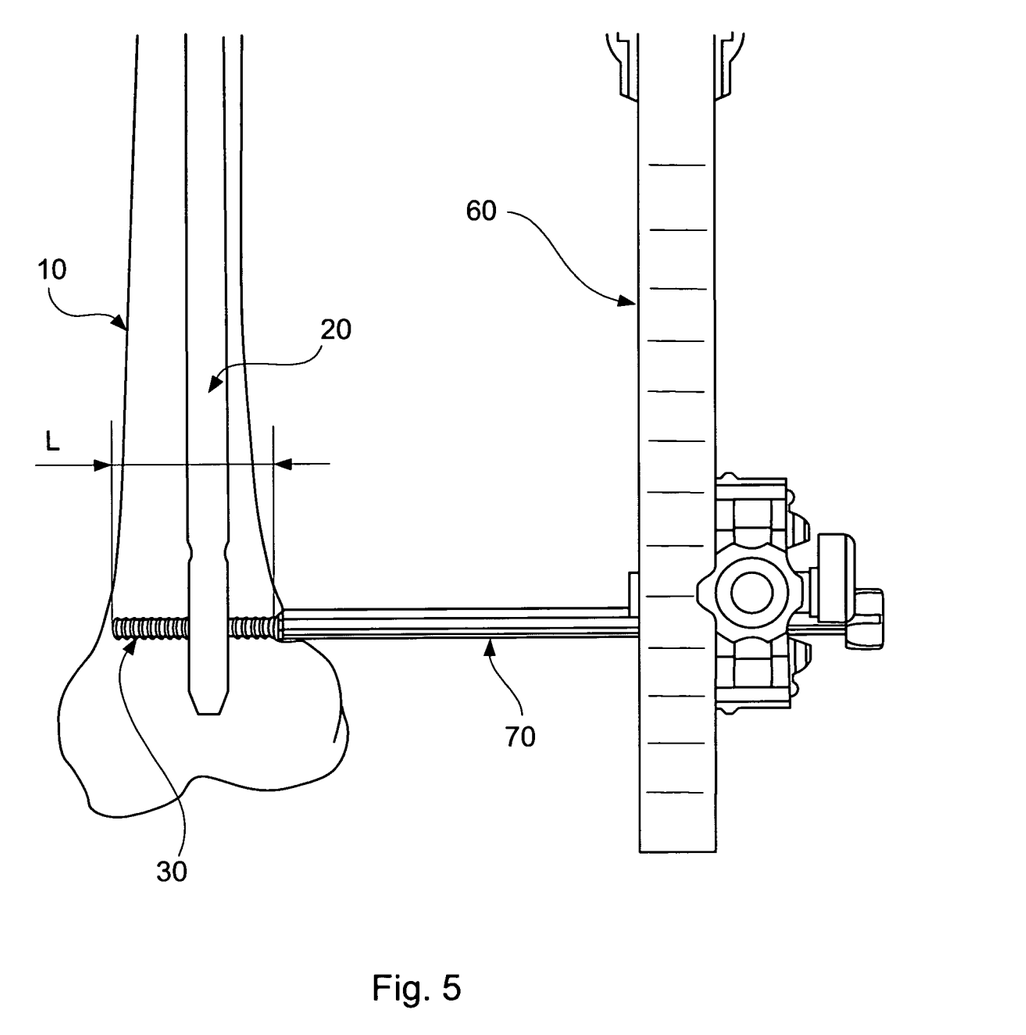
FIG. 5 shows a bone together with a screw imaged from a second direction.

FIGS. 3 to 5 illustrate an embodiment of a method, wherein the method is performed to determine a length of a screw which should be inserted through a lateral bore of a bone nail at a distal end of a femur.

FIG. 3 shows a schematically visualization of an X-ray image (encircled) together with a bone model. The X-ray image is a 2D projection image of a distal end portion of a femur 10, generated in a medial-lateral direction. A bone nail 20 is located within the medullary channel of the femur 10. The tip 22 of the bone nail 20 is located in the femur with a distance D away from the most distal point of the femur 10. With a distance X from the tip 22 of the bone nail 10, a center of a bore 24 through the bone nail 20 is provided. In this example, it is assumed that a locking screw should be inserted through bore 24.

In the X-ray image of FIG. 3, the bone nail 20 may serve as a reference body. For example the actual amount of the distance X is known so that a scale factor can be calculated based on the actual distance X and on the distance X as measured in the X-ray image. Accordingly, the actual distance which corresponds to the distance D as imaged may be determined utilizing the scale factor.

Furthermore, the diameter of the femur, for example measured perpendicular to the axis of the femur or the axis of the bone nail, is measured in the X-ray image so as to determine the actual diameter of the femur shaft at a distinct distance from the most distal point of the femur. Based on the determined actual diameter, a corresponding bone model 50 can be selected and, if necessary, adapted to the determined actual diameter of the femur.

At the selected bone model, a plane or slice may be identified through which a screw should be inserted. This plane or slice 56 may be identified in a distance D+X measured from the most distal point at the bone model of the femur, with the known distance X and the determined distance D. A plan view of the identified slice 56 is shown in FIG. 4.

In FIG. 4, the 2D projection image of FIG. 3 is shown again, but with an indication of the longitudinal axis 26 of the bone nail 20 and the center line 16 of the shaft of the femur 10. As can be seen, the bone nail is located within the upper half of the femur. The slice 56 is shown in FIG. 4 with the center line of the slice being identical to the center line in the X-ray projection image next to it, and with the axis of the bone nail being identical to the axis 26 of the bone nail 20 in said X-ray projection image.

Based on the center line 16 of the femur shaft and the axis 26 of the bone nail, a height H can be determined at which the screw is to be inserted through the femur, thus extending through the transverse bore of the bone nail. It is noted that the height, i.e. the position of the bore measured in an anterior-posterior direction, may also be determined relative to one of the outer surfaces of the femur instead of the center line thereof.

As can be seen in the illustration of the slice 56 of the bone model, the outer contour of the bone is not regular. In particular, the distance between two opposite outer surfaces vary depending on the position and/or angle at which the distance is measured. Accordingly, the horizontal width L in the height H differs from the width $L_{max}$ which would be recognizable in an X-ray image generated in a vertical direction, i.e. perpendicular to the width. In fact, the width L is smaller than the width $L_{max}$.

In FIG. 5, only a schematically X-ray projection image is shown, wherein this X-ray image is generated in an anterior-posterior direction, i.e. from above when the person is lying on his/her back.

FIG. 5 shows the femur 10, the bone nail 20 as well as an aiming device 60, wherein a tissue protection sleeve 70 is arranged at the aiming device. The tissue protection sleeve 70 may serve firstly as a reference body for the determination of a further scale factor, secondly as a guide element for guiding a drill which is used to drill a channel for a screw through the bone, and thirdly as a means for allowing the screw to be accurately inserted into the drilled bore without interfering with surrounding tissue. It will be understood that also the bone nail 20 and alternatively the arm of the aiming device 60 may serve as a reference body for determining the further scale factor.

As depicted in FIG. 5, the length of the screw is smaller than the overall width of the bone as visualized in the X-ray projection image. However, the length of the screw is appropriate for an introduction at the intended position (distance to distal end of bone and height relative to bone axis) and in the intended direction.

While embodiments has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures cannot be used to advantage.

The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

LIST OF REFERENCE SIGNS

10 femur
16 center line of femur shaft
20 bone nail
22 tip of bone nail
24 transverse bore
26 axis of bone nail
30 screw
50 bone model
52 medullary channel of bone model
54 Corticalis of bone model
56 slice of bone model
60 aiming device
70 tissue protection sleeve
100 processing means
200 imaging device
220 C-arm
240 X-ray source
260 X-ray detector
300 input device
400 monitor
500 region of interest
600 database

The invention claimed is:

1. A method for identifying a length of a bone screw to be inserted through a bore drilled in a predetermined drilling direction at a predetermined position through a bone, the method comprising:
    identifying the predetermined drilling direction and the predetermined position in a first X-ray image of the bone, transferring the identified direction and position to a corresponding bone model, wherein the identification of the predetermined position at the bone includes a measurement of distances between the bore and an outer surface of the imaged bone (i) in an axial direction of the bone and (ii) in a direction perpendicular to the axial direction of the bone, and
    determining the length of the bone screw based on the transferred direction and position at the bone model.

2. The method of claim 1, further comprising the step of determining a diameter of the imaged bone between two opposed outer surfaces of the imaged bone in relation to a reference body visible in the first X-ray image.

3. The method of claim 2, further comprising the step of determining a diameter of the imaged bone between two opposed outer surfaces of the imaged bone in relation to the reference body in a second X-ray image of the bone, wherein imaging directions of the first X-ray image and the second X-ray image differ from each other.

4. The method of claim 1, further comprising the step of selecting a bone model from a group of bone models with different sizes and shapes, the selected bone model corresponding to the imaged bone.

5. The method of claim 1, further comprising the step of adapting the bone model so that the bone model corresponds to the imaged bone.

6. The method of claim 1, wherein the first X-ray image is generated in a direction being parallel to the drilling direction.

7. The method of claim 1, wherein the length (L) of the bone screw corresponds to a distance between the outer surfaces of the bone at two ends of the bore.

8. The method of claim 1, wherein the bone screw is a locking screw adapted to be inserted through a lateral bore of a bone nail.

9. A method for identifying a length of a bone screw to be inserted through a bore drilled in a predetermined drilling direction at a predetermined position through a bone, the method comprising:

taking a first x-ray image of the bone and of a reference body visible in the first x-ray image;

identifying the predetermined drilling direction and the predetermined position in the first X-ray image of the bone, wherein the identification of the predetermined position at the bone includes a measurement of distances between the bore and outer surface of the imaged bone (i) in an axial direction of the bone and (ii) in a direction perpendicular to the axial direction of the bone;

selecting a bone model from a database containing a group of human bone models with different sizes and shapes, the selected bone model being the bone model in the database most closely corresponding to the imaged bone;

transferring the identified direction and position to the selected bone model; and determining the length of the bone screw based on the transferred direction and position from the bone model.

10. The method of claim 9, further comprising determining a diameter of the imaged bone between two opposed outer surfaces of the imaged bone in relation to the reference body visible in the first X-ray image.

11. The method of claim 9, wherein the first X-ray image is generated in a direction being parallel to the drilling direction.

12. The method of claim 9, wherein the length (L) of the bone screw corresponds to a distance between the outer surfaces of the bone at two ends of the bore.

13. The method of claim 9, wherein the bone screw is a locking screw adapted to be inserted through a lateral bore of a bone nail.

* * * * *